United States Patent [19]
Snider

[11] 4,256,960
[45] Mar. 17, 1981

[54] INSTRUMENT AND METHOD FOR CALIBRATING NUCLEAR CAMERAS
[75] Inventor: David M. Snider, New Berlin, Wis.
[73] Assignee: General Electric Company, Schenectady, N.Y.
[21] Appl. No.: 60,442
[22] Filed: Jul. 25, 1979
[51] Int. Cl.³ .................. G12B 13/00; H03K 5/153; G01T 1/20
[52] U.S. Cl. .................. 250/252; 250/363 S; 307/362
[58] Field of Search .................. 250/252, 363 S, 366, 250/214 C; 307/362, 363, 364

[56] References Cited
U.S. PATENT DOCUMENTS
4,079,257 3/1978 Jatteau et al. .................. 250/252

Primary Examiner—Alfred E. Smith
Assistant Examiner—Carolyn E. Fields
Attorney, Agent, or Firm—Ralph G. Hohenfeldt

[57] ABSTRACT

An instrument for tuning the photomultiplier (PM) tubes of a scintillation camera to the gamma ray photon energy spectrum of interest. A finely collimated beam of photons from a test isotope is placed on the scintillator crystal in alignment with the photomultiplier tubes in succession. A summing amplifier develops signals that are proportional to the total energy of scintillation events. Lower and upper level discriminators define an energy window and produce output signals, respectively, depending on whether incoming total energy signals are within or above the window level. The output signals are sent to an integrating capacitor. A sensing circuit continuously senses capacitor voltage and drives visual indicators which indicate whether the energy spectrum within the acceptable window predominates or whether energies above the window predominates and the gain of the PM tube under test is adjusted accordingly.

11 Claims, 8 Drawing Figures

INSTRUMENT AND METHOD FOR CALIBRATING NUCLEAR CAMERAS

This invention relates to an improved method and instrument for tuning gamma cameras of the type used in nuclear medicine. The invention is particularly applicable to gamma ray photon sensitive cameras similar to the well-known Anger gamma camera which is disclosed in U.S. Pat. No. 3,011,057.

In nuclear medicine, gamma cameras are used to detect gamma ray or other high energy photons emitted from a body in which a radioisotope has been infused. The photons are emitted in correspondence with the extent to which the isotope is absorbed by the tissue under examination. The emitted photons are absorbed in a crystalline material and scintillation events occur at the points of absorption. Most absorption events are substantially congruent with the point from which the photons are emitted from the body, since the photons are directed to the scintillation crystal with a collimator. An array of photomultiplier (PM) tubes, generally hexagonally arranged, are optically coupled to the scintillator crystal so that each tube will produce an output signal whose magnitude depends on its particular geometrical relationship to the event being detected and to its energy. The position of each PM tube is signified by its cartesian or x and y coordinates. The signals from each tube are supplied to a resistor weighting matrix which enables computing the x and y coordinates of each event. The signals corresponding with the coordinates are used to drive a cathode ray tube display or other type of display such that an intensity change is made or written at the coordinate point in the display screen which desirably corresponds with the true coordinates of the scintillation event. Conventionally, the energy of each event is summed and subjected to pulse height analysis. If the total energy falls within the window of the analyzer, a z pulse is produced which unblanks the display to write the light spot. A photographic film may be used as an integrator of the large number of points or spots of light appearing on the screen of the display. A substantial number of scintillation events is required to make up the final picture or radioactivity distribution in the body tissue which defines the infused organ.

One of the objectives in gamma photon imaging systems is to obtain uniformity in the displayed image. For instance, if a test disk containing a uniformly distributed radioisotope is placed in view of the camera for a predetermined time interval, the displayed image should be composed of uniformly distributed light spots or points having substantially uniform brightness. As is well-known, however, gamma cameras have inherent characteristics, which unless compensated, result in nonuniformity that is manifested by excessively dense, and hence, bright zones in the image and by excessively sparse, and hence, dark zones in the image. Several different kinds of circuits have been proposed and are in use for correcting nonuniformity and substantial progress has been made.

A prerequisite to adjusting a gamma camera system for maximum uniformity, even though additional electronic correction circuits are used, is to tune the photomultiplier tubes, which means that their gains must be adjusted so they have maximum response to the photon energy peaks for the isotope being used and minimum response to other parts of the energy spectrum.

As is well-known, tuning the PM tubes can be a very laborious process which, up to the present, has required use of bulky, expensive and complicated instruments which are often not readily available and require a high degree of skill to use. One PM tube tuning method involves use of a multichannel analyzer for comparing the outputs of the tubes. Other methods are available too. Most of them require expenditure of two to four or more hours, depending on the number of PM tubes in the particular camera, which is especially undesirable if retuning has to be done where the gamma camera is installed.

SUMMARY OF THE INVENTION

Objects of the present invention are to provide a photomultiplier tube tuning instrument which can be easily incorporated in new gamma cameras or retrofitted to existing cameras and which enables tuning to be accomplished accurately, quickly, easily and with minimal skill being required.

In accordance with the new tuning apparatus and method, a radioisotope test source constituting a point source is used to direct a sharply collimated beam of gamma photons into the scintillator. Typically, the source may cause 5,000 scintillation events per second to be detected by the scintillator. During tuning, the point source is moved from the center of one PM tube to the center of an adjacent tube during the tuning procedure and, in one embodiment of the invention, a tuning indicator comprised of light emitting diodes is observed while the source is in a given location. If the PM tube under test is indicated to be mistuned, its gain control potentiometer is adjusted until a proper tuning indication is observed. When all PM tubes have been tested once, the procedure is repeated to account for the fact that adjusting the gain of any tube affects the output of the other tubes to a minor extent.

The new calibrating instrument uses a window type pulse height analyzer (PHA) which may be the one that is usually present in gamma cameras system of the type under consideration. The PHA receives analog voltage pulses whose amplitudes are proportional to the sum of the different amplitudes of the signals from all of the PM tubes and is, therefore, proportional to the total energy (E) of each photon absorption event or scintillation. Two trains of analog output pulses in separate channels are obtained from the PHA. The pulses in one train correspond with E pulses whose energy peaks fall within the window, that is, between the lower level (LL) and upper level (UL) limits of the window. The pulses in the other train correspond with E pulses whose peaks have amplitudes higher than the upper level of the window. These pulses set and reset an electronic switch such as a flip-flop whose Q output goes high and low depending on whether the triggering E pulse is above or within the window, respectively. The flip-flop output connects to an integrating capacitor which charges a little for pulses above the UL and discharges a little for pulses within the window, that is, between LL and UL, so the voltage on the capacitor is indicative of the quantity of E signals falling within the window. The capacitor signal amplitude is continuously sensed by a comparator whose output goes high and low depending on the instantaneous capacitor voltage. The comparator drives a pair of gates, each of which control light sources such as a light emitting diode (LED). The operator observes the two LED's going on and off. This calls for adjusting the particular PM tube under test until both lights just toggle slowly, but with the lower level light being on most of the time although there will still be a little activity above the window. Balance or proper gain setting is indicated by both diodes flickering slowly.

A more detailed description of the new calibration method and an illustrative embodiment of the new calibrating instrument will now be set forth in reference to the drawings.

DESCRIPTION OF THE DRAWINGS

FIG. 7 is a graph of total energy pulse duration versus pulse energies; and

DESCRIPTION OF A PREFERRED EMBODIMENT

Figures 1, 8:
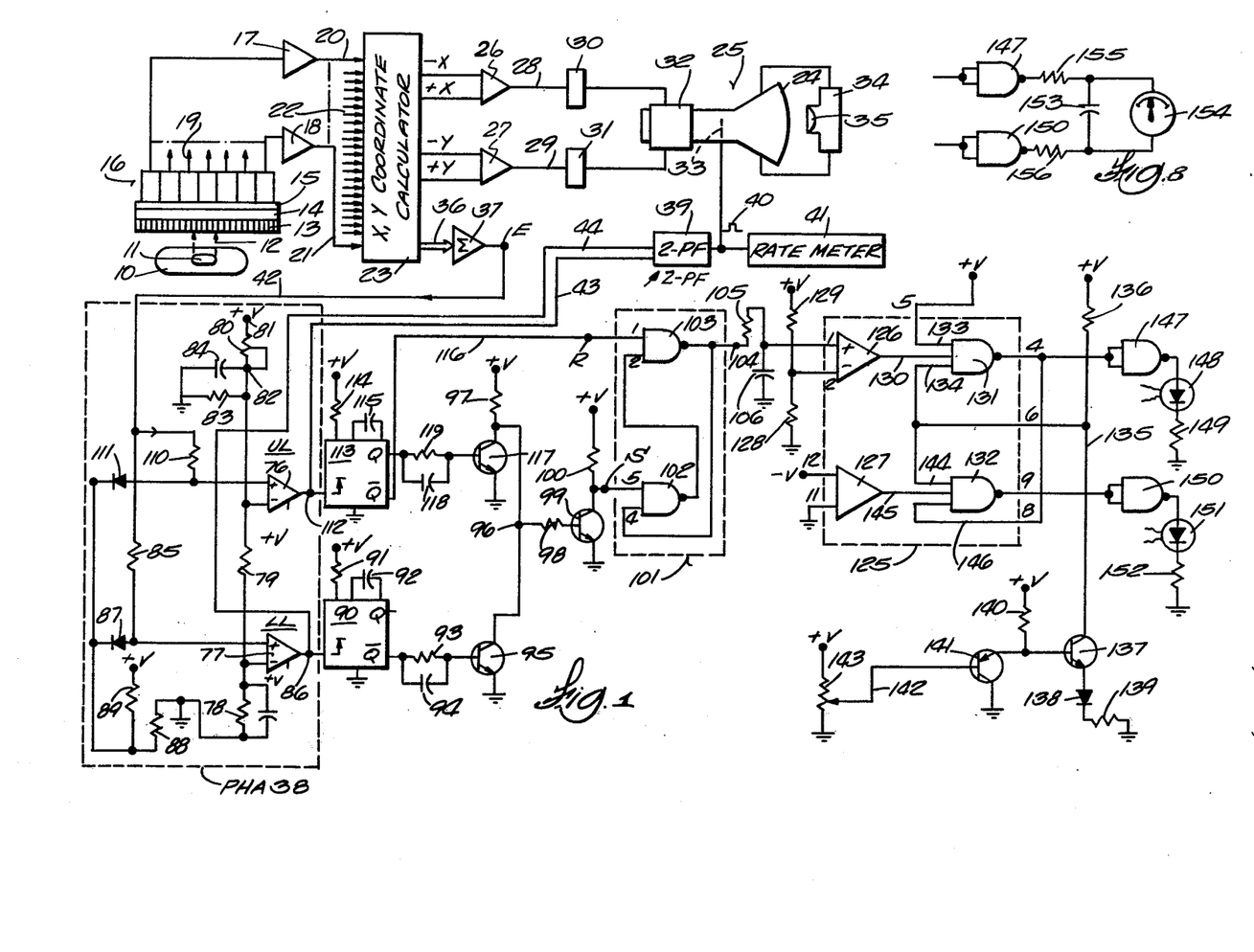
FIG. 1 is a block diagram of a gamma camera system and a more detailed circuit diagram of the new calibrating instrument.
FIG. 8 is an alternative form of gain setting indicator, using a meter, and which is adapted for use in the calibrating instrument depicted in FIG. 1.

The principal components of a conventional gamma camera system of the Anger type will be briefly outlined first in reference to FIG. 1 to provide the necessary background for describing the new calibration instrument.

Referring to FIG. 1, a body which is to be examined with the gamma camera is designated by the reference numeral 10. An organ of the body 11 may be infused with any of several radioactive isotopes used in nuclear medicine for gamma ray imagining such as $Tc^{99}$ which has a half-life of six hours and has a photon energy peak at 140 KEV although there are some photons in a spectrum ranging as low as 50 KEV and as high as 500 KEV. $Co^{57}$ is a suitable isotope for use as a test source during PM tube tuning or calibration. It has an energy peak at about 122 kiloelectron volts (KEV) although it may emit or there may be background radiation present having energies well above and below the peak energy of interest. $Co^{57}$ has a half-life of 270 days and is not used as a clinical nuclide.

Figures 1, 2, 3, 4, 5, 6:
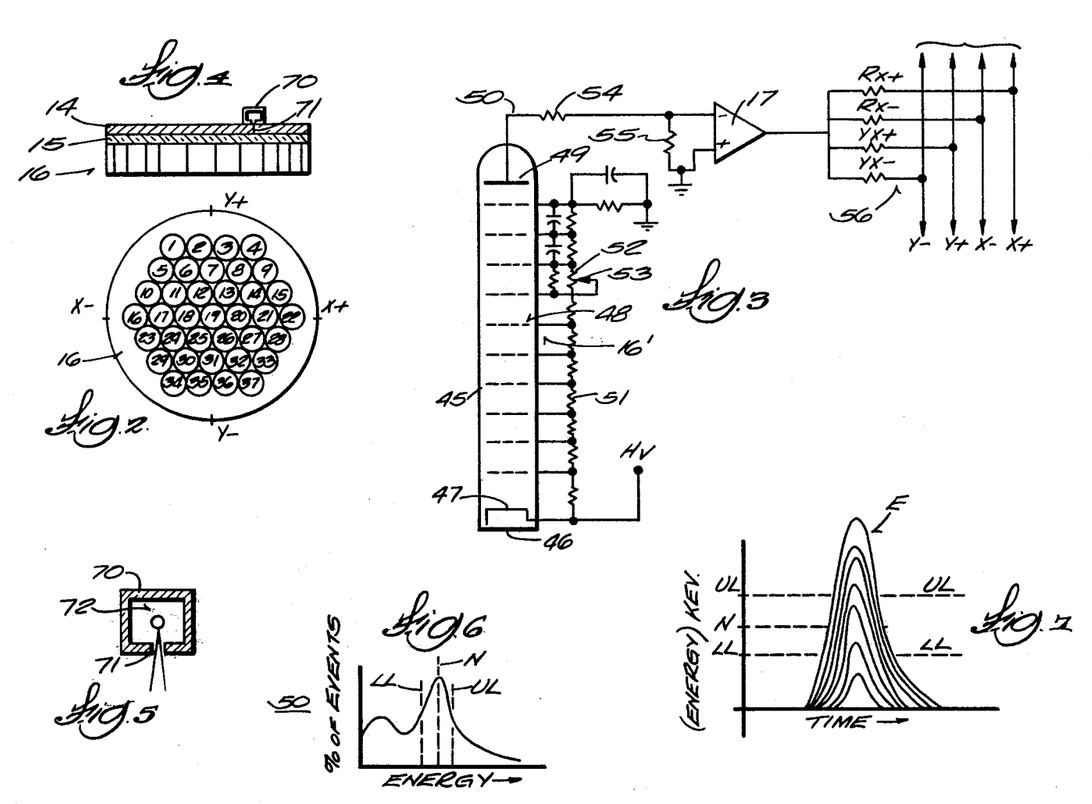
FIG. 2 is a plan view of a photomultiplier tube array used in a gamma camera.
FIG. 3 is a diagram of a photomultiplier tube and one of the resistor networks used in the calculator which determines the x and y coordinates of scintillation events and provides signals which can be used to obtain a total energy signal summation.
FIG. 4 is a diagram of the gamma camera head when it is being used in the calibration mode.
FIG. 5 is a diagram of a radioisotope point source which is used during the calibrating procedure.
FIG. 6 is a graph of photon energy versus the percentage of photons or scintillation events which are likely to have a particular energy.

The isotope infused organ 11 emits gamma ray photons which are used to delineate the structure of the organ. Properly directed photons are indicated by the dashed line arrows 12. These photons pass through a collimator 13 and are absorbed in a scintillator crystal 14 where photon absorptions produce scintillations. The scintillations are coupled by means of a glass plate 15 to the lower input ends of an array of photomultiplier (PM) tubes which are collectively designated by the reference numeral 16. Each scintillation event is detected by every PM tube and each PM tube produces an output signal whose amplitude is dependent on the energy of the scintillation and the geometrical relationship between the tube and the scintillation event. The camera used to exemplify the new PM tube tuning instrument has 37 PM tubes in array 16, but various numbers of tubes may be used in gamma cameras such as 19, 37, 61, or 91 tubes. The PM tube arrangement is shown in FIG. 2. The new tuning instrument can be used with any of them.

The output signals from the anodes of each PM tube are supplied to the inputs of preamplifiers of which there is one for each PM tube. Only two preamplifiers, marked 17 and 18, are shown but it will be understood that all of the output lines from PM tubes such as the one marked 19 lead to preamplifiers.

The individual energy signals on output lines 20 and 21 of preamplifiers 17 and 18 and those on lines such as the group marked 22 from the other preamplifiers are supplied to a calculator circuit which is symbolized by the block marked 23. As can be seen in FIG. 2, the PM tube array 16 has a central tube 19 which is at the intersection of x and y axes. The location of each PM tube can be identified by its coordinates and so can the scintillations. As is well-known, a fundamental object is to display the scintillation events at corresponding coordinates on the screen 24 of a cathode ray display tube 25 in true correspondence with the coordinates of the events in the scintillator 14. Thus, calculator 23 in FIG. 1 produces signals corresponding with the $-x$ and $+x$ coordinates and $-y$ and $+y$ coordinates or cartesian coordinates which are summed in amplifiers 26 and 27 which yield the net x and y coordinate signals on their output lines 28 and 29. These signals are supplied to respective deflection amplifiers 30 and 31 which drive the electrostatic x and y deflection plates 32 of cathode ray tube 25. If the total energy of a scintillation event falls between the upper and lower limits of the window of a pulse height analyzer 38, a z pulse signal is simultaneously applied to control electrode 33 of cathode ray tube 25 to thereby unblank the tube and cause a light point or spot to be written on its screen 24 at coordinates corresponding with those of the scintillation event as determined by calculator circuit 23. The light spots are integrated on a film in a camera 34 which views screen 24 through its lens 35. Because the radioisotope is distributed in the organ 11 differentially, in due course, a corresponding differential distribution of the light spots will be integrated on the film and the organ becomes defined or imaged.

Continuing with the description of the conventional parts of an Anger type gamma camera, all of the energy signals from all of the PM tubes for every scintillation are delivered by way of a bus 36 to a summing amplifier 37 on whose output the total energy signal E is obtained, this signal being proportional in amplitude to the total energy of the scintillation event. The total energy signal or E signal is supplied by way of line 42 to a pulse height analyzer which is enclosed in the dashed line rectangle marked PHA 38. PHA 38 has lower and upper level discriminators LL and UL, as will be discussed more fully later, operative to pass E signals having an energy above a lower window limit, LL, and to reject signals that are above the upper window limit, UL. The output terminals of PHA 38 are marked 112 and 86 and they connect to the input of a conventional z-pulse former circuit, shown as a block marked 39 and Z-PF, by way of lines 43 and 44, respectively. Accepted E pulses trigger the z pulse former 39 to produce a z pulse 40 which is delivered to control electrode 33 of the cathode ray tube to unblank it and cause it to write a light spot on its screen. A ratemeter, symbolized by the block 41 is also usually present in systems of this type to provide information on E pulse rate which is used for various purposes, not shown.

Before discussing the remainder of FIG. 1, that is, before discussing the new calibration method and instrument which is depicted therein, some other relevant matters will be reviewed. Refer to FIG. 6. It shows a typical plot of the spectrum of photon energies received by the gamma camera versus the percentage of events that are likely to have a particular energy. The highest percentage of events corresponds with the dominant or peak energy characteristic, marked N, of the isotope with which the body organ is infused. The dominant energy band falls between lower energy limit LL and upper energy limit UL. The limits define a window or spectral band which is acceptable for producing light spots on the cathode ray tube screen and, hence, for contributing to the image of the organ.

FIG. 7 shows a family of total energy signals, E, resulting from various scintillations. One may see that they are polyenergetic. As is well-known, this is so because no isotope produces is only one unique line or spectral peak and it further results from the fact that there is electronic noise and background radiation such as from cosmic rays and man-made radiation. Thus, it is only those total energy pulses whose peaks are within the window between UL and LL which are considered valid and acceptable for use to form the organ image. The theoretical characteristic peak is about at the energy level marked N.

Other factors to be considered before discussing the new calibrator are exemplified in FIG. 3. This figure shows a typical PM tube 16' comprised of an evacuated envelope 45 having a scintillation or light input window 46 which, as was explained in connection with FIG. 1, is optically coupled to scintillator crystal 14 by means of glass plate 15. This typical PM tube has a photocathode 47 to which a high voltage, typically 1 to 2 kilovolts below ground, is applied. The PM tube has a plurality of dynodes or intermediate electrodes 48 that cause electron multiplication and yield electrons which are directed to anode 49 on which the output signal is developed corresponding with scintillation energy, on its output line 50. The dynodes have potential distributing resistors such as those marked 51 connected between them. One group of resistors including resistor 52 is made variable or as a potentiometer whose arm 53 is movable to enable adjusting the gain of the PM tube. This potentiometer is adjusted during the calibration or tuning procedure with the new instrument as will be explained.

FIG. 3 also shows a typical preamplifier 17, corresponding with one similarly marked in FIG. 1, to whose non-inverting input the signals from the PM tube are coupled through a divider comprised of resistors 54 and 55. The output of representative preamplifier 17 is supplied to one of the resistor networks 56 which is present in x, y coordinate calculator 23 in FIG. 1. There is a resistor network, not shown, for each of the PM tubes. As is customary, the values of the resistors in the networks are weighted so that they jointly correspond with the x and y coordinates of the PM tube which supplies them with energy signals. All of the $-x$ and $+x$ and $-y$ and $+y$ signals outputted from the respective networks are combined to produce the $+x$ and $-x$ and $+y$ and $-y$ output signals from the calculator which are supplied to summing amplifiers 28 and 29 in FIG. 1 as is conventional.

As indicated earlier, the sum of all of the network signals is also formed by summing amplifier 37 and constitutes the total energy or E signal which is supplied to PHA 38 by way of line 42 in FIG. 1.

FIG. 5 shows a test isotope source which is used for calibrating. Basically, it comprises a box with a lining composed of radiation shielding materials 70 such as lead. The box has a collimating pin hole 71 in one wall. Suspended in the center of the box is a small radioactive source which would contain an isotope which is comparable to the isotope used in the body organ examinations for which the gamma camera is being set up or calibrated. The isotope source is marked 72. Some gamma ray photons from source 72 are radiated in all directions and undergo reflections before emerging from collimator pin hole 71. Some reflected photons may undergo Compton modified scattering which means that they will lose energy before they are projected through collimator pin hole 71. Some photons will emerge directly through hole 71. There will be a natural spectrum of energies in the photons which form the fine beam that emerges from hole 71 but the greatest percentage of photons will fall within upper and lower energy spectrum limits as explained in connection with FIGS. 6 and 7.

FIG. 4 shows the main elements of the gamma camera set up in preparation for carrying out the calibration procedure. Note that the collimator 13 has been removed and the test source 70 is placed directly on scintillator crystal 14 with its collimated pin hole 71 aimed for projecting a gamma ray photon beam into scintillator crystal 14 for producing the rapidly recurring scintillations which are detected by the array 16 of PM tubes. It is desirable to have the scintillator crystal 14 scribed with marks that indicate the centers of the respective PM tubes. The test source is placed over the PM tube centers during the calibration procedure. As mentioned earlier, the gain of the PM tube with which the test source is aligned is adjusted in accordance with the observed indications of the new calibrator circuit and then the test source is moved to an adjacent PM tube and the process is repeated until all tubes have been tested and their gains have been adjusted.

A specific description of the new calibration method and instrument will now be given in reference to FIG. 1. Assume that test source 70 of FIG. 5 is in place over one of the PM tubes and that pulse signals, corresponding with total energy, E, of each scintillation event, are being delivered from summing amplifier 37 to line 42 which is the input line to the pulse height analyzer, PHA 38. There will be E pulses having a variety of total energies as indicated in FIG. 7. The pulse rate or frequency of scintillation events might be 5,000 counts per second for a fresh isotope sample but could be lower if the source has cycled through several of its half-lives. Some isotopes may produce higher count rates and others may produce lower rates.

In FIG. 1, the total energy analog pulses or E pulses are delivered to PHA 38 by way of line 42 to an upper level (UL) discriminator based on a threshold comparator amplifier 76 and to a lower level (LL) discriminator based on a threshold comparator amplifier 77. The inverting inputs of these amplifiers are connected to a bias voltage divider comprised of series connected resistors 78, 79, 80 and 83. Resistor 80 is adjustable to permit establishing the upper level of the energy window and providing variable window width control. The divider is supplied from a voltage source input terminal 81 and the voltage which is to be divided is developed at junction 82 between resistor 80 and a grounded resistor 83 that is in parallel with an a-c bypass capacitor 84. The analog E pulses are processed by each discriminator 76 and 77 simultaneously. One path of the E pulses is to lower level or threshold discriminator 77 through an input resistor 85 which is connected to the non-inverting input of threshold amplifier 77. Any input signal which is above threshold, that is, above the lower window limit LL at its inverting input, will produce a corresponding output signal on the output line 86 of amplifier 77. Diodes 87 and 111 and resistors 88 and 89 constitute a clamping circuit which assures that any overvoltages due to excessive energies will not adversely effect comparators 76 and 77. Comparator amplifiers 76 and 77 may be type 75207 dual line receivers but other types could be used.

For every E pulse above the lower level discriminator 77 threshold level, an output signal appears on output terminal 86 and this constitutes the input or trigger terminal of a one-shot multivibrator 90 insofar as PM tube calibration is concerned. Multivibrator 90 produces output pulses whose durations are determined by timing resistor 91 and capacitor 92. In an actual embodiment, an output pulse of 1.4 microseconds duration is generated for every incoming trigger pulse from comparator 77. The $\bar{Q}$ output terminal of one-shot multivibrator 90 is normally high in this example and goes to a low logic level when there is an incoming trigger pulse. The $\bar{Q}$ output pin of one-shot multivibrator 90 is connected through a resistor 93, paralleled with a speed-up capacitor 94, to the base of a transistor 95. When the $\bar{Q}$ output is high, that is, in the absence of an incoming trigger pulse, the collector to emitter path of transistor 95 is conducting and its collector is effectively grounded. When the $\bar{Q}$ output goes low due to a triggering E pulse having energy above LL threshold, transistor 95 turns off and its collector voltage, appearing at junction point 96 goes high. The collector of transistor 95 is connected to one end of a pull-up resistor 97 which is supplied from a d-c source. Thus, when transistor 95 turns off, junction point 96 goes high or more positive. The positive pulses produced at junction point 96 by E pulses above LL threshold or the lower energy limit are coupled through a resistor 98 which is the base resistor of a normally nonconducting transistor 99. This transistor has a collector resistor 100 supplied from a d-c source. When there is an accepted E pulse such that point 96 goes high, transistor 99 turns on and its collector goes low. This collector is connected to the set input of an RS flip-flop 101 which is comprised of a pair of cross connected NAND gates 102 and 103.

The set input pin of RS flip-flop 101 is marked S, its reset signal input pin is marked R and its output pin is marked 104. Output pin 104 is coupled through a resistor 106 to an integrating capacitor 106. For every E pulse above LL threshold and within the window, output pin 104 goes low and causes capacitor 106 to discharge a little. Because capacitor 106 may also be recharging at a particular rate, as will be explained, it will be evident that the voltage level on capacitor 106 will be related to the rate at which acceptable above threshold E pulses are coming in. By way of example, and not limitation, resistor 105 may have a value of 10 kilohms and the capacitor a value of 33 microfarads. Pulse rates at output pin 104 on the order of 3,000 to 10,000 Hz are illustrative but the pulse rates will depend on the disintegration rate of the particular isotope being used in the test.

The total energy pulses, E, from summing amplifier 37 are also delivered to the input of the upper level discriminator, UL, channel concurrently with being delivered to the lower level discriminator channel which has just been described. Thus, the E pulses are conducted by way of line 42 through an input resistor 110 to the non-inverting input of comparator 76. The clamping or overvoltage protective circuit comprising diode 111 and the biasing divider which includes resistors 88 and 89 has been mentioned previously. Any E pulse having energy above the upper window limit, UL, will cause comparator 76 to produce an analog pulse signal on its output terminal 112 which connects by way of line 43 to z pulse former 39 for image production purposes as mentioned earlier. For calibration purposes, terminal 112 also connects to the trigger terminal of another one-shot multivibrator 113. The output pulse duration of this multivibrator is governed by the values of resistor 114 and capacitor 115. By way of example, and not limitation, in an actual embodiment, the pulse duration has been set at 2.5 microseconds.

The $\bar{Q}$ output terminal of multivibrator 113 is connected, by way of line 116, to the reset signal input pin, marked R, of RS flip-flop 101. Thus, for every incoming E pulse which is above the upper window limit, UL, causes flip-flop 101 to reset which means that its output pin 104 goes to a high logic voltage state. This results in adding a small amount of charge to integrating capacitor 106 to increase its voltage and thereby offset some of the voltage by which capacitor 106 has been decreased due to discharging in response to E signals which are within the window and are derived from the previously described lower level discriminator channel. Thus, it will be seen that the voltage on integrating capacitor 106 will go up and down during the calibration procedure depending on whether the E pulses are predominantly above the upper level of the energy window or predominantly within the window and, therefore, representative of the desired peak energy.

The Q output pin of multivibrator 113 is connected through a resistor 119 to the base emitter circuit of a transistor 117. Resistor 119 has a speed-up capacitor 118 in parallel with it. The Q pin of one-shot multivibrator 113 is in a low voltage state in the absence of any incoming E trigger pulses which are within or above the window. Thus, the collector to emitter circuit of transistor 117 is normally non-conductive. When there are incoming E pulses which are above the upper window limit, the Q pin switches to a high state and this causes transistor 117 to become conductive. When transistor 117 conducts, its collector voltage goes to ground level and junction point 96 goes to ground, thereby preventing transistor 99 from conducting. Of course, junction point 96 would also have a tendency to go high as a result of the same E pulse being coupled through the lower level discriminator, but its pulses cannot be coupled to the set pin S of flip-flop 101 because the collector of transistor 95 is effectively grounded by virtue of point 96 being grounded through transistor 117. This makes charging and discharging integrating capacitor 106 mutually exclusive, that is, only incoming E pulses which exceed the upper window limit will contribute to charging integrating capacitor 106 and only those E pulses which are between the lower limit, LL, and upper limit, UL, will contribute to discharging capacitor 106.

During the PM tube calibration or tuning mode, the remainder of the circuitry continuously senses the voltage on integrating capacitor 106 and provides a visual indication as to whether most of the incoming E pulse peaks are within the energy band that corresponds with the peak energy of the isotope being used. If such is not the case, the gain of the PM tube under test with test source 70 at the moment is adjusted, as required, with its gain control potentiometer 52 as in FIG. 3, until the condition is met.

The first stage of the sensing and indicating circuit constitutes an integrated circuit dual line receiver which is used as a voltage comparator 125 and is all on one chip as indicated by the dashed line rectangle shown in FIG. 1. In an actual embodiment, by way of example and not limitation, a type Ser. No. 75207 integrated circuit was used. It has two comparator amplifiers 126 and 127. Integrating capacitor 106 is coupled to the non-inverting input of comparator 126. The reference voltage, applied to the inverting input of comparator 126, is obtained from a voltage divider including series connected resistors 128 and 129 which are connected between supply voltage and ground. It will be evident that the output line 130 of comparator 126 will swing to its high voltage state when the voltage on integrating capacitor 106 is above the comparator reference voltage and that output line 130 will be in its low logic voltage state when the voltage on integrating capacitor 106 is below reference level. This provides a comparison of the rates at which E pulses within the window and above the upper window limit are coming in. As indicated earlier, the gain of the PM tube under test is tuned or adjusted until the low energy pulses or pulses within the window predominate. However, there are usually some relatively high energy pulses coming through at all times because there will be ambient high energy photons within the camera view due to cosmic rays. In a hospital there could be stray high energy photon flux due to x-ray equipment, nearby radioisotope therapy equipment, or from stored isotopes in a nuclear medicine laboratory as examples.

Integrated circuit 125 also has two inverters in the form of NAND gates 131 and 132. Gate 131 has three inputs marked 130, 133 and 134. Input 133 is always at a high logic level or enabled by reason of it being connected to a d-c source. Input 130 goes high and low depending on the integrator capacitor 106 voltage which is proportional to the frequencies at which the LL and UL representative pulses are coming in. Input 134 of gate 131 is switched to a high state during the calibration mode to fully enable gate 131. Thus, input 134 is connected by way of pin 6 of integrated circuit 125 to a line 135 which connects to a resistor 136 that is supplied from a d-c source. Line 135 also connects to the collector of a transistor 137 whose emitter is connected to ground through diode 138 and resistor 139. When the calibration mode is not in effect, transistor 137 is allowed to be conductive so as to pull input 134 of gate 131 down to ground level and disable gate 131. Resistor 136 acts as the collector pull-up resistor of transistor 137. Its emitter biasing resistor is marked 140. It supplies bias current to transistor 137 unless another transistor 141 is turned on. Transistor 141 is turned on to permit enabling gate 131 for the calibration mode by sliding the arm 142 of a potentiometer 143 to ground, thereby turning transistor 141 on and removing the biasing current from the base of transistor 137. As stated, this results in gate 131 being enabled.

Inverting NAND gate 132 in integrated circuit 125 has one of its inputs 144 held high in the calibration mode, by virtue of being connected to line 135, so that inverting NAND gate 132 is enabled during the calibration mode. Another input 145 to gate 132 is derived from the output of comparator amplifier 127 which serves as a reference and is normally high. The other input 146 of gate 132 is cross connected from pin 8 to pin 4 which is the output pin for the other gate 131. Thus, when the output pin 4 of gate 131 goes high, corresponding with input E pulses predominantly being within the window, input 146 of gate 132 goes low and its output pin 9 goes high.

Output pin 4 of gate 131 is connected to the inputs of an inverter 147. The output of this inverter leads to a light emitting diode (LED) 148 in series with a resistor 149 which is connected to ground. Thus, when the input to inverter 147 is low its output is high and LED 148 turns on. This means that incoming E pulses are predominantly above the upper window limit. When the inputs to inverter 147 are high, its output is low and LED 148 is off meaning that incoming E pulses are predominantly within the window.

Another inverter 150 also has an LED 151 and a resistor 152 in its output circuit. The inputs of inverter 150 connect to pin 9 of integrated circuit 125 which is the output pin of NAND gate 132. When the output of gate 131 goes high, it triggers gate 132 to produce a low logic level signal on its output pin 9 which signal is coupled to the input of inverter 150. By reason of inversion, this causes the other diode 151 to flash on. Conversely, LED 151 is turned off when incoming E pulses are predominantly above the window. This indicates to the operator that the gain of the PM tube under test should be reduced in which case diode 148 will begin to go off, indicating that more E pulses are falling within the window.

To summarize, the incoming pulses to integrating capacitor 106 corresponding with those within the window are usually coming in at a high rate such as 5 kHz, depending upon the test isotope being used, and E pulses corresponding with energies above the window are usually coming in at a lesser rate. Because of integration, the flashing rates of LEDs 148 and 151 will be low enough for the eye to perceive them. If LED 148 is off most of the time, it is an indication that incoming E pulses are predominantly within the window. If LED 151 is on most of the time, the same is true. On the other hand, if LED 148 is on most of the time and LED 151 is off more of the time, it means that incoming E pulses are predominantly above the window and that the gain of the PM tube under test should be reduced.

Proper adjustment is indicated when LED 151 is on most of the time, indicating that incoming E pulses are predominantly within the window and LED 148 is flashing on occasionally as it should be since there is always some aberrant high energy stray radiation in the camera field whose indication should not be totally eliminated because it would result in the gain of the PM tube being set so low that some E pulses in the acceptable energy range would fall below the threshold of input lower level comparator 77.

From the viewpoint of the operator, calibration is a simple procedure. The finely collimated gamma ray photon beam from test source 70 is simply set on scintillator crystal 15 and aligned with one PM tube after another while their gains are being adjusted. The operator then only has to watch the LED indicators and make gain adjustments which result in LED 151 being on most of the time with the other LED 148 flashing on occasionally. It is suggested that the center group of 19 PM tubes in FIG. 2 be calibrated first followed by the six corner tubes and 12 edge tubes in the illustrative 37 tube array and a comparable sequence should be followed when the camera has other numbers of PM tubes. The test sequence should be carried out at least twice to negate the effects of interaction between the PM tubes in the calculating circuit resistor network as was discussed earlier.

The circuit described above uses discrete LEDs 148 and 151 for a visual indication of the PM tube gain settings. They do not have to be discrete, they could be, as in the actual instrument, the decimal points of LED displays which are used for other purposes which are not effectuated during the calibration mode. Although light sources such as LEDs 148 and 151 are considered to be the better way of indicating gain settings to the calibrating technician, other indicating means have been used successfully but their cost is greater. For instance, as in FIG. 8 the two gates, 147 and 150 which correspond with those similarly marked in FIG. 1, could alternately charge and discharge another integrating capacitor 153 through resistors 155 and 156, which capacitor is connected across any suitable analog meter such as a milliammeter 154. This meter has its needle zeroed at the center of the scale and swings to the left or right depending on which E pulse energy level is prevailing.

As implied earlier, two versions of the new PM tube tuning or calibrating instrument are available. One is a small portable free standing instrument that can be retrofit temporarily or permanently to existing gamma cameras and the other version is an instrument which is built into the gamma camera at the time of manufacture.

Existing gamma cameras and, of course, newly manufactured ones too will have a pulse height analyzer comparable to PHA 38 for providing signals at lower level discriminator output terminal 86 and upper level discriminator output terminal 112. Generally, these analog output signals will be sufficiently strong to drive a z-pulse former such as Z-PF 39 but may not be strong enough to drive the calibrator circuit. Therefore, the multivibrators 113 and 90 or gates are used as TTL signal level changers in the retrofit version and it becomes compatible with any existing pulse height analyzer such as PHA 38. In other words, the trigger signal input pins of multivibrators 113 and 90 are the signal inputs to the retrofit version and they connect, respectively, to the output terminal 112 of UL discriminator 76 and output terminal 86 of LL discriminator 77. As explained earlier, these multivibrators trigger RS flip-flop 101 which might be considered the first stage of the basically new calibration or tuning indicator circuit.

The pulse forming circuit Z-PF 39 in new camera designs include means that are functionally equivalent to multivibrators 113 and 90 and to the switching transistors 117, 99 and 95 so the output signals from the pulse forming circuit are available at TTL levels. Thus for the version which is built into the gamma camera at the time of manufacture, signals corresponding with those fed to the R and S pins of flip-flop 101 in the FIG. 1 embodiment can be fed into the R and S pins directly from pulse forming circuit and the additional multivibrators and intervening transistors become unnecessary.

Although the method and an embodiment of the instrument for tuning a gamma camera have been described in considerable detail, such description is intended to be illustrative rather than limiting, for the invention may be variously embodied and is to be limited only by interpretation of the claims which follow.

I claim:

1. An instrument for calibrating the gain of photomultiplier tubes in a gamma ray photon responsive camera, said camera comprising a scintillator for producing scintillation events in response to absorption of said photons, an array of adjustable gain photomultiplier tubes optically coupled to said scintillator and operative to produce simultaneous analog output signals having amplitudes corresponding to that part of the energy in an event which the particular tube detects, means for summing said signals resulting from each event to produce a total energy analog signal proportional in amplitude to the total energy in an event, the calibration mode of said camera involving projecting a beam of gamma ray photons from a test radioisotope into said scintillator in alignment with the tube under test, said instrument comprising:

integrating capacitor means,
means responsive to occurrence of total energy signals which have peak amplitudes above a predetermined lower energy limit by changing the voltage level on said capacitor means by a predetermined amount in one direction and responsive to occurrence of total energy signals which have peak amplitudes above a predetermined upper energy limit by changing the voltage level on said capacitor means by a predetermined amount in the opposite direction, said upper and lower limits defining an energy window,
means for sensing the voltage on said integrating capacitor means and indicating means for providing one indication of the voltage on said capacitor means being below a predetermined level and for providing another indication of the voltage on said capacitor means being above said predetermined level to thereby indicate how the gain of the photomultiplier tube under test should be adjusted for the total energy signal peaks to fall predominantly within said window.

2. An instrument for calibrating a scintillation camera, said camera comprising a scintillator for producing scintillations in response to absorption of gamma ray photons, a plurality of photomultiplier tubes optically coupled to said scintillator and operative to produce simultaneous electric analog signals, respectively, whose amplitudes are dependent on the energies of the absorbed photons and on the geometrical relationship of a tube to an absorption event when a beam of photons from a test radioisotope is projected into said scintillator in alignment with a tube, means operative to sum said analog signals and produce total energy signals proportional in amplitude to the total energy of said absorption events, means for adjusting the gains of the respective photomultiplier tubes, first discriminator means having input means for receiving said total energy signals and having output means, said first discriminator means being operative to produce first output signals in response to total energy signals which have peak amplitudes above a predetermined lower energy limit,
second discriminator means having input means for simultaneously receiving said total energy signals and having output means, said second discriminator means being operative to produce second output signals in response to total energy signals which have peak amplitudes above a predetermined upper energy limit, said lower and upper energy limits defining an energy window, said calibrating instrument comprising:

integrating capacitor means, means for adding an incremental charge to said capacitor means to increase the voltage on it exclusively in response to occurrence of output signals from one of said discriminator means and for subtracting an incremental charge from said capacitor means to decrease the voltage on it exclusively in response to occurrence of output signals from the other of said discriminator means, means for sensing the voltage on said integrating capacitor means and indicating means for providing one indication of the voltage on said capacitor means being below a predetermined level and for providing another indication of the voltage on said capacitor means being above said predetermined level to thereby indicate how the gain of the photomultiplier tube under test should be adjusted for the total energy signal peaks to fall predominantly within said window.

3. The instrument as in claim 1 wherein said indicating means are comprised of individual light sources.

4. The instrument as in claim 1 wherein said indicating means comprises an analog type meter.

5. The instrument as in claims 2, 3 or 4 wherein said means for adding and subtracting charge to and from said integrating capacitor means includes flip-flop means having an output terminal coupled to said capacitor means and being responsive to occurrence of said output signals from one of said discriminator means by switching its output terminal to a high voltage state for charging said capacitor means and being responsive to occurrence of said output signals from the other of said discriminator means by switching its output terminal to a lower voltage state than said high voltage state for discharging said capacitor means.

6. An instrument for calibrating a scintillation camera, said camera comprising a scintillator for producing scintillations in response to absorption of gamma ray photons, a plurality of photomultiplier tubes optically coupled to said scintillator and operative to produce simultaneous electric analog signals, respectively, whose amplitudes are dependent on the energies of the absorbed photons and on the geometrical relationship of a tube to an absorption event when a beam of photons from a test radioisotope is projected into said scintillator in alignment with a tube, means operative to sum said signals and produce total energy signals proportional in amplitude to the total energy of said absorption events, means for adjusting the gains of the respective photomultiplier tubes, first discriminator means having input means for receiving said total energy signals and having output means, said discriminator means being operative to produce an output signal in response to input of each total energy signal whose peak amplitude is above a predetermined lower energy limit, second discriminator means having input means for receiving said total energy signals and having output means, said second discriminator means being operative to produce an output signal in response to input of each total energy signal whose peak amplitude is above a predetermined upper energy limit, said upper and lower energy limits defining an energy window, said calibrating instrument comprising:

first triggerable means having an output terminal and responding to being triggered by an output signal from said first discriminator means by producing a signal level change having a predetermined duration on its output terminal, second triggerable means having an output terminal and responding to being triggered by an output signal from said second discriminator means by producing a signal level change having a predetermined duration on its output means, integrating capacitor means, gate means having output means coupled to said integrating capacitor means, said gate means responding exclusively to signal level changes on the output terminal of one of said triggerable means by increasing the voltage on said capacitor means during one of the predetermined durations and responding exclusively to signal level changes on the output terminal of the other of said triggerable means by decreasing the voltage on said capacitor means during the other of the predetermined durations, means for sensing the voltage on said integrating capacitor means and indicating means for providing one indication of the voltage on said capacitor means being below a predetermined level and for providing another indication of the voltage on said capacitor means being above said predetermined level to thereby indicate how the gain of the photomultiplier tube under test should be adjusted for the total energy peaks to fall predominantly within said window.

7. The instrument as in claim 6 wherein said indicating means are comprised of individual light sources.

8. The instrument as in claim 6 wherein said indicating means comprises an analog type meter.

9. The instrument as in claim 6 including means for inhibiting said gate means from changing the voltage on said capacitor means in response to a signal on the output terminal of one said triggerable means corresponding with a total energy signal being above said lower limit if there is a simultaneous signal on the output terminal of the other of said triggerable means corresponding with said total energy signal being above said upper limit.

10. The instrument as in any of claims 6, 7, 8 or 9 wherein said means for sensing the voltage on said capacitor means is a comparator having input means for the voltage on said capacitor and input means for a reference voltage and output means for providing signals corresponding with the capacitor voltage being above and below said reference voltage, respectively, said indicating means including a pair of gates each having a plurality of inputs and each having an output, the output of one gate being connected to one input of the other gate, means for applying a signal to one of the inputs of one gate and simultaneously to one of the inputs of the other gate to enable the gates during a test, means for applying fixed level signals to another of the inputs of said one gate and another of the inputs of said other gate to further enable said gates, one of the inputs of said one gate being coupled to the output of said comparator and said one gate being responsive to signals corresponding to said capacitor voltage being above said reference voltage by changing the voltage level on its said output, said other gate being responsive to signals corresponding to said capacitor voltage being below said reference voltage by changing the voltage level on its output, additional gate means coupled, respectively, to the outputs of said one and said other gates, said additional gates each having output means and being responsive to voltage level changes on the output of said one and said other of said gates, respectively, by changing the voltage levels on the outputs of said additional gates, said indicating means further comprising light emitting devices coupled to said output means of said additional gates.

11. A method of testing and calibrating the gain of each photomultiplier tube in a scintillation camera comprising the steps of:

directing a beam of photons from a radioisotope source into the scintillator to which the photomultiplier tubes are optically coupled and in alignment with a tube that is to be tested, said radioisotope producing photons having a broad spectrum of energies including a preferred spectral band or window defined by lower and upper energy limits, summing the analog output signals from each tube resulting from photon absorption events in the scintillator to obtain total energy analog signals whose amplitudes are proportional to the total energies of successive events, producing a first series of pulses of predetermined amplitude and duration in correspondence with each total energy signal amplitude peak that is above said lower energy limit and within said window and concurrently producing a second series of pulses of predetermined amplitude and duration in correspondence with each total energy signal amplitude peak which is above said upper energy limit and above said window, adding an increment of charge to an integrating capacitor to thereby raise its voltage in correspondence with occurrence of each pulse in one series and subtracting an increment of charge from said capacitor to thereby lower its voltage in response to occurrence of each pulse in the other series, continuously sensing the voltage on said integrating capacitor and providing indicating means to indicate, respectively, if the sensed voltage is above or below a predetermined value to thereby enable a determination as to whether total energy signals within said window or above said window predominates so that the gain of the photomultiplier tube under test may be adjusted to make total energy signals falling within said window predominate.

* * * * *